(12) United States Patent
Grande et al.

(10) Patent No.: US 11,820,752 B2
(45) Date of Patent: Nov. 21, 2023

(54) PROCESS FOR THE PREPARATION OF APALUTAMIDE

(71) Applicant: OLON S.P.A., Rodano (IT)

(72) Inventors: Valentina Grande, Rodano (IT); Gabriele Ferretti, Rodano (IT); Barbara Novo, Rodano (IT)

(73) Assignee: OLON S.P.A., Rodano (IT)

( * ) Notice: Subject to any disclaimer, the term of this patent is extended or adjusted under 35 U.S.C. 154(b) by 0 days.

(21) Appl. No.: 17/059,551

(22) PCT Filed: May 27, 2019

(86) PCT No.: PCT/IB2019/054371
§ 371 (c)(1),
(2) Date: Nov. 30, 2020

(87) PCT Pub. No.: WO2019/229625
PCT Pub. Date: Dec. 5, 2019

(65) Prior Publication Data
US 2021/0206742 A1 Jul. 8, 2021

(30) Foreign Application Priority Data
May 30, 2018 (IT) ........................ 102018000005874

(51) Int. Cl.
*C07D 401/04* (2006.01)
*C07C 237/30* (2006.01)
*C07C 327/24* (2006.01)
*C07F 7/18* (2006.01)

(52) U.S. Cl.
CPC .......... *C07D 401/04* (2013.01); *C07C 237/30* (2013.01); *C07C 327/24* (2013.01); *C07F 7/1896* (2013.01); *C07C 2601/04* (2017.05); *C07C 2601/16* (2017.05)

(58) Field of Classification Search
CPC .................................................. C07D 401/04
See application file for complete search history.

(56) References Cited

U.S. PATENT DOCUMENTS

| 10,513,504 B2 * | 12/2019 | Apotex ................ C07D 207/40 |
| 2015/0094296 A1 | 4/2015 | Tsukamoto et al. |
| 2016/0229814 A1 | 8/2016 | Yamamoto et al. |
| 2018/0141914 A1 | 5/2018 | Frigoli et al. |

FOREIGN PATENT DOCUMENTS

| CN | 107501237 A | 12/2017 |
| CN | 108047200 A | 5/2018 |
| CN | 108069869 A | 5/2018 |
| WO | 2008119015 A2 | 10/2008 |
| WO | 2018014802 A1 | 1/2018 |

OTHER PUBLICATIONS

Shukla, Raj. "New Automated Purification Strategies for Scale-Up." Seqens. (Dec. 25, 2017). Accessed Jan. 28, 2022. (Year: 2017).*
American Chemical Society. Chemical Abstract Service. RN 2230023-72-8. First available to public: Jul. 5, 2018. (Year: 2018).*
Pang X et al., "Design, synthesis, and biological evaluation of deuterated apalutamide with improved pharmacokinetic profiles," Bioorganic & Medicinal Chemistry Letters, vol. 27, No. 12, Apr. 26, 2017, pp. 2803-2806.
Search Report and Written Opinion of PCT/IB2019/054371 dated Aug. 1, 2019.
Chinese Office Action dated Aug. 2, 2023 in connection with counterpart Chinese Patent Application No. 20198003469.3.

* cited by examiner

*Primary Examiner* — John S Kenyon
(74) *Attorney, Agent, or Firm* — SILVIA SALVADORI, P.C.; Silvia Salvadori

(57) ABSTRACT

The present invention relates to a process for the preparation of Apalutamide of formula (A) Apalutamide is a latest-generation androgen receptor inhibitor, used to treat non-metastatic castration-resistant prostate cancer.

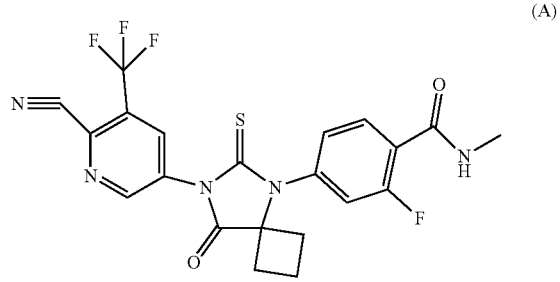

(A)

6 Claims, No Drawings

PROCESS FOR THE PREPARATION OF APALUTAMIDE

This application is a U.S. national stage of PCT/IB2019/054371 filed on 27 May 2019, which claims priority to and the benefit of Italian Application No. 102018000005874 filed on 30 May 2018, the contents of which are incorporated herein by reference in their entireties.

FIELD OF INVENTION

The present invention relates to a process for the preparation of Apalutamide of formula:

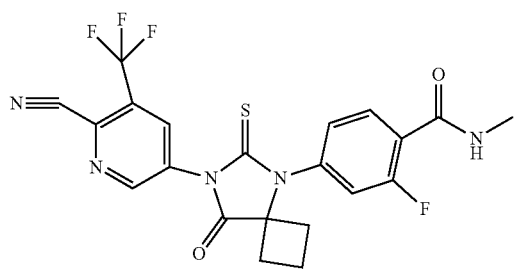 [SMILES: CNC(=O)c1ccc(N2C(=S)N(c3cnc(C#N)c(C(F)(F)F)c3)C(=O)C23CCC3)cc1F]

Apalutamide is a latest-generation androgen receptor inhibitor, used to treat non-metastatic castration-resistant prostate cancer.

PRIOR ART

WO2007126765 discloses the synthesis of Apalutamide by reacting the compound of formula V

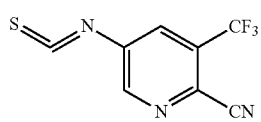

with the compound of formula:

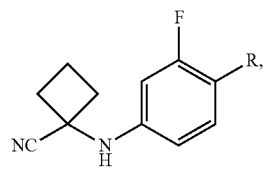

followed by hydrolysis. Said process is difficult to scale up industrially, as it involves the use of microwaves at 80° C. for 20 h.

WO2008119015 and WO2011103202 disclose processes for the synthesis of Apalutamide, always characterised by a large number of reactions and the use of an intermediate requiring a hydrolysis step, which reduces the yields and economy of the process.

CN108069869 A describes the alkylation of 4-halogen-2-fluoro-N-methylbenzamide with 1-aminocyclobutane-1-carboxylic acid to give 4-[(1-carboxycyclobutyl)amino]-2-fluoro-N-methylbenzamide, followed by esterification of carboxylic acid, as reported in scheme 1 below.

Scheme 1

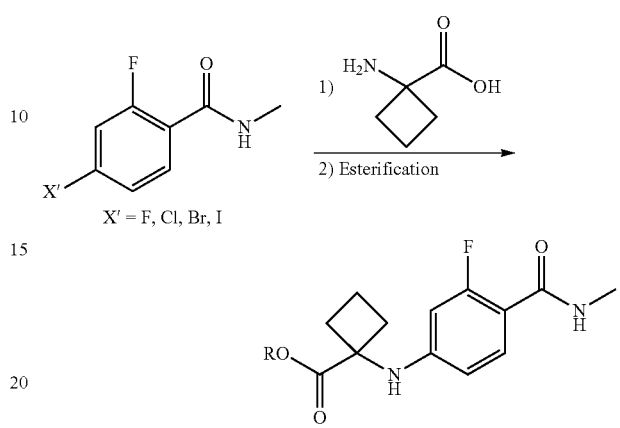

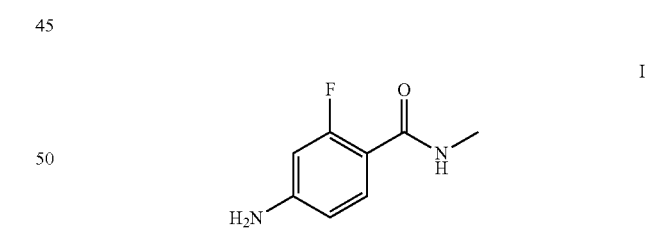

The resulting product is reacted with compound V to give Apalutamide.

DESCRIPTION OF THE INVENTION

A process for the preparation of Apalutamide has now been found which is more advantageous than the known processes as it does not require hazardous, difficult to manage reagents such as potassium cyanide, thiophosgene and the like, or expensive catalysts, leading to cost savings and a lower environmental impact.

The synthesis scheme of the process of the invention is shown below:

The process according to the invention comprises:

(a): alkylation of 4-amino-2-fluoro-N-methylbenzamide of formula I

I

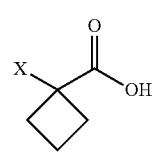

with an alkyl halide of formula II

II

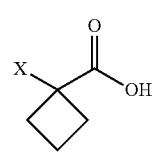

wherein X is chlorine, bromine or iodine, preferably bromine, to give the compound of formula III

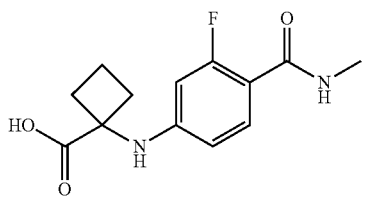

III (b): activation of the carboxyl function of the compound of formula III, via the formation of the compounds of formula IV

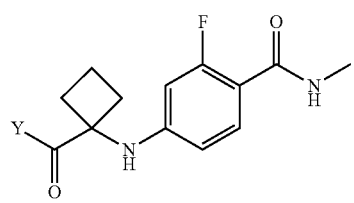

IV wherein Y is a carboxyl-activating group;
(c): condensation of the activated product IV obtained in step (b) with the isothiocyanate of formula V

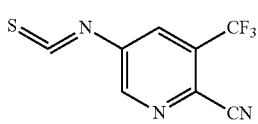

(V)

to give crude Apalutamide;
(d): purification of the crude Apalutamide obtained in step (c).

The first step involves alkylation of an amine with an alkyl halide, namely alkylation of Intermediate I, 4-amino-2-fluoro-N-methylbenzamide, by an intermediate II, such as 1-bromocyclobutane-1-carboxylic acid.

Said alkylation is selective, and does not give rise to the formation of impurities deriving from multiple attachments and/or to the production of a quaternary amine salt. The reaction yield and purity of the product are therefore not prejudiced, and Intermediate III is isolated as a crystal with good yields and very high purity without further purifications.

Said alkylation process is advantageous over the one disclosed in CN 108069869 A (Scheme 1), which involves reacting intermediate I, containing a halogen atom instead of the amino group, with intermediate II, wherein X is equal to NH₂.

The reactivity of an amino group on a cyclobutane ring is different from that of an amino group on a benzene ring, and the ease of removal of an aryl halide is also different from that of an alkyl halide. It has surprisingly been found that by reversing the position of the nucleophilic amino group, comparable results are obtained in terms of yield as indicated in the comparative examples, but by a process better suited to industrial application.

The reaction conditions in step a) of the process of the invention involve the use of only 7 volumes of solvent as against the 27 described in CN 108069869 A, and the reaction is conducted at the temperature of 60-65° C. as against 100° C., the number of reaction hours being equal.

Moreover, the reagents used in the process according to the invention, (4-amino-2-fluoro-N-methyl benzamide I, 1-bromocyclobutan-1-carboxylic acid II and 5-isothiocyanate-3-(trifluoromethyl)-2-pyridincarbonitrile V, are commercially available. Example 1 describes the reaction, reproduced on the same scale as described in CN 108069869 A, paragraph [0077], p. 7.

The second step of the process of the invention consists in condensation between the carboxyl function of Intermediate III and a suitable nucleophile able to form a stable activated carboxylic acid derivative IV. Examples of preferred derivatives are alkyl esters, aryl esters, thioesters and silyl esters. Examples of said esters are intermediates IVa, IVb, IVc and IVd.

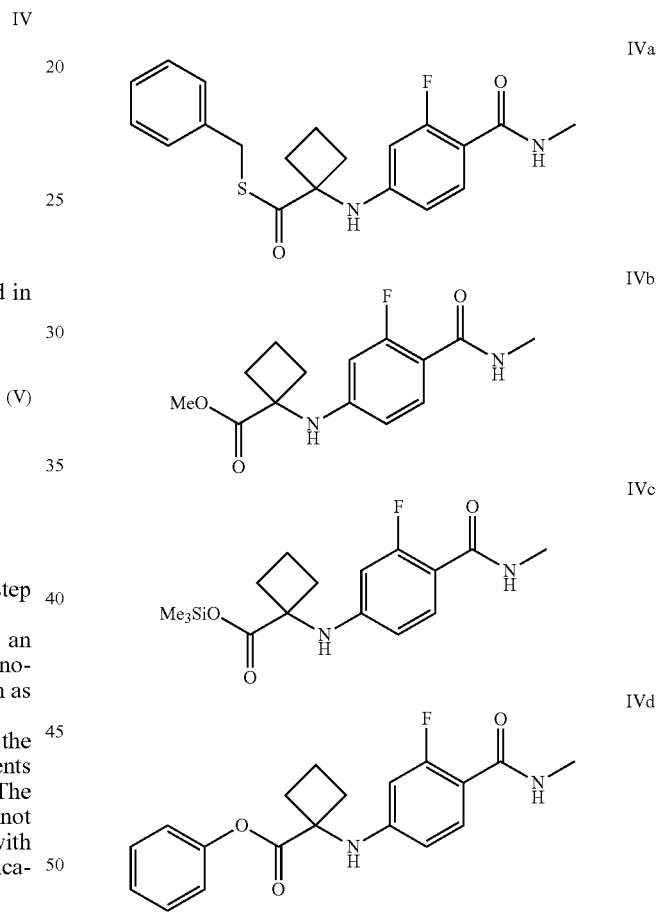

Said esters can be isolated or used "as such", without isolation, in the subsequent reaction.

The third step of the process of the invention consists in the preparation of Apalutamide by cyclisation between derivatives IV and intermediate V. The resulting crude Apalutamide is purified and isolated (step d).

The intermediates of formulae IVa, IVc and IVd are novel, and are a further object of the invention. Their use is advantageous as it makes no use of hazardous and environmentally harmful reagents.

The process of the invention has the considerable advantage of closing the thioxo-imidazoline ring in a single step, with no need for further functionalisations, hydrolysis to amides or deprotections.

DETAILED DESCRIPTION OF THE INVENTION

Step (a): Alkylation of 4-amino-2-fluoro-N-methylbenzamide I with 1-bromocyclobutan-1-carboxylic acid II The reaction is conducted in polar aprotic solvents in the presence of a base, at temperatures ranging from 20 to 100° C., preferably from 40 to 80° C., most preferably between 55 and 65° C.

The reaction can be conducted using dioxane, tetrahydrofuran (THF) or 3-methyl-tetrahydrofuran as solvent, preferably dioxane.

The base can be organic or inorganic, preferably organic. Triethylamine is preferred.

The reaction is conducted in a stoichiometric ratio of compound II to compound I ranging from 1 to 2, preferably from 1.2 to 1.8, most preferably from 1.4 to 1.6.

The reaction time is from 10 to 40 hours, preferably from 20 to 30 hours.

To isolate intermediate III, the reaction mixture is left to cool at room temperature, to obtain a precipitate. The product, obtained as carboxylate salt, is dissolved or suspended in a polar protic solvent such as water, methanol or ethanol, preferably water, and converted to free acid by adding a strong acid such as hydrochloric acid, hydrobromic acid or sulphuric acid, preferably hydrochloric acid, until a pH of from 1.5 to 3.5, preferably between 2 and 3, is obtained. The product precipitates and is isolated as free acid in a good yield and high purity.

Step (b): Activation of Intermediate III

Intermediate III is preferably activated as thioester, such as benzyl thioester IVa, as alkyl ester, such as methyl ester IVb, as silyl ester, such as trimethylsilyl ester IVc, or as aryl ester, such as phenyl ester IVd.

For derivatisation to thioesters, dichloromethane, toluene or dimethylformamide (dMF) can be used as solvent, preferably dichloromethane. The reaction can be catalysed with bases, preferably dimethylamino pyridine. The derivatised product is isolated as a crystal.

The derivatisation to ester, such as methyl ester IVb, can be conducted in solvents such as alcohols, dichloromethane, toluene, dimethyl carbonate (dMC) or dimethylsulphoxide (dMSO), preferably DMC or DMSO.

The reaction can be catalysed with bases, preferably potassium carbonate.

The derivatised product is isolated as a crystal.

The derivatisation of intermediate III as silyl ester, for example trimethylsilyl ester IVc, is conducted in polar solvents such as dichloromethane or dioxane, or solvent-free, preferably solvent-free in the presence of silylating reagents.

Examples of silylating reagents which can be used to prepare trimethylsilyl ester IVc include trimethylsilyl chloride, bis(trimethylsilyl)acetamide and hexamethyldisilazane, preferably hexamethyldisilazane. The reaction is conducted at a temperature ranging from 15 to 110° C., preferably from 60 to 105° C., most preferably from 90 to 100° C.

The reaction is conducted in a stoichiometric ratio of silylating agent to Intermediate III ranging from 1.5 to 10, preferably from 3 to 9, most preferably from 5 to 8.

When using some silylating reagents an acid such as trifluoroacetic acid, hydrochloric acid, hydrobromic acid, etc. must be used to activate the reaction, preferably trifluoroacetic acid; with other silylating reagents a base such as pyridine, triethylamine, diisopropylamine, etc. must be used to neutralise the hydrohalic acid formed, preferably pyridine.

The reaction time is from 4 to 20 hours, preferably from 10 to 18 hours, most preferably from 12 to 16 hours. After a suitable solvent change, the product can be isolated as a crystal.

Intermediate III can also be derivatised as aryl ester, for example as phenyl ester IVd; solvents such as dimethylacetamide, dimethylformamide, dioxane and dimethylsulphoxide, preferably dimethylsulphoxide, can be used for said derivatisation. The reaction can be catalysed with bases such as $KHCO_3$, DBN, DBU, DMAP and TBD, preferably DBN. The reaction is conducted in a stoichiometric ratio of base to intermediate III ranging from 0.05 to 1 equivalent, preferably from 0.05 to 0.5, most preferably 0.1 equivalents. The reaction is conducted at a temperature ranging from 15 to 110° C., preferably from 60 to 105° C., most preferably from 90 to 100° C.

The reaction time is from 4 to 22 hours, preferably from 12 to 22 hours, most preferably from 15 to 20 hours.

The derivatised product is isolated as a crystal.

Step (c): Coupling Between Intermediates IVa-d and Intermediate V

The reaction is conducted in various solvents such as acetonitrile, ethyl acetate, isopropyl acetate, isobutyl acetate, dimethylsulphoxide, dimethylformamide (dMF), etc., preferably dimethylsulphoxide, most preferably a mixture of isopropyl acetate and dimethylsulphoxide.

The reaction is conducted at temperatures ranging from 40 to 120° C., preferably from 60 to 110° C., most preferably from 80 to 100° C.

The reaction is conducted in a stoichiometric ratio of intermediate IVa-d to intermediate V ranging from 1 to 2, preferably from 1.2 to 1.8, most preferably from 1.3 to 1.6.

The reaction time is from 10 to 60 hours, preferably from 15 to 40 hours, most preferably from 20 to 30 hours.

The crude Apalutamide product, after a suitable work-up, can be purified by crystallisation or other known techniques.

The process will now be further illustrated by the following examples.

Example 1: Synthesis of Intermediate III

Compound I (20 g, 0.119 mol) is suspended in 140 mL of dioxane. TEA (50 mL, 0.359 mol) is added by pouring in a thin stream. The system is placed under nitrogen, and heated to 60° C. A solution of intermediate II (32 g, 0.179 mol) in 60 mL of dioxane is prepared separately.

The solution of compound II is added to the suspension in the reactor and left to react for about 20 hours. The mixture is then cooled to 15° C. and filtered through a Büchner funnel, washing the cake twice with 20 mL of dioxane each time. The resulting product is suspended in 240 mL of water, 1M HCl is added until a pH<3 is reached, and the resulting suspension is then filtered through a Buchner funnel, washing the cake twice with 40 mL of water each time.

The crystal thus isolated is dried under vacuum at the temperature of 60° C., providing intermediate III in a 65% yield (20.5 g, 77.3 mmol) and 99.6% HPLC purity.

$^1$H NMR (300 MHz, $CDCl_3$) δ 15.3 (m, 4H), 2.58 (t, br, 2H), 2.73 (s, 3H), 6.00 (m, 1H), 6.22 (s, 1H), 7.17 (s, 1H), 7.46 (s, 1H), 7.65 (d, 1H), 12.63 (m, 1H).

Example 2: Synthesis of Intermediate IVa

Intermediate III (20 g, 75 mmol) is suspended in 120 mL of dichloromethane and cooled to 0-5° C. When said temperature is reached, benzyl mercaptan (12.6 mL, 106.7 mmol) is added by pouring in a thin stream, ensuring that the temperature does not exceed 5° C.

A solution of dicyclohexylcarbodiimide (dCC) (17 g, 82.4 mmol) in 40 mL of dichloromethane is prepared separately. The resulting solution of DCC is then dripped onto the suspension of intermediate III, ensuring that the temperature does not exceed 7° C. When the addition is finished, DMAP (145 mg, 1.2 mmol) is added and the mixture is heated to a temperature of 20-25° C., and left to react for about 17 hours. 130 mL of water and 100 mL of a 14% solution by weight of sodium hypochlorite are added, without exceeding 30° C., and the mixture is left under stirring for 8 hours.

The resulting two-phase mixture is filtered through a Buchner funnel, washing the cake twice with 20 mL of dichloromethane each time; the solid can be discarded. The phases are separated, and the organic phase is washed three times with 160 mL of water each time.

The resulting organic phase undergoes a solvent change with toluene; an abundant precipitate forms, and is left to cool slowly overnight. The precipitate is filtered through a Büchner funnel, washing the cake with 30 mL of toluene. The crystal thus isolated is dried under vacuum at the temperature of 60° C., providing intermediate IVa in a 78% yield (22 g, 59 mmol) and 95% HPLC purity.

$^1$H NMR (300 MHz, CDCl$_3$) δ 1.80-2.25 (m, 4H), 2.56 (m, 2H), 2.72 (d, 3H), 4.02 (s, 2H), 6.00-6.20 (dd, 2H), 7.27 (m, 5H), 7.50 (m, 2H), 7.16 (t, br, 1H).

Example 3: Synthesis of Intermediate IVb

Intermediate III (20 g, 75 mmol) is dissolved in 200 mL of DMSO, and dimethyl carbonate (50 mL, 594 mmol) and potassium carbonate (4.15 g, 30 mmol) are added; the system is placed under nitrogen and heated at 90° C. for 22 h. It is then cooled to room temperature, 200 mL of dichloromethane and 250 mL of water are added, the mixture is left under stirring for 10 minutes, and the phases are separated. The aqueous phase is extracted with 100 mL of dichloromethane. The combined organic phases are washed with 250 mL of water, and concentrated to residue; the residue is taken up with 100 mL of toluene and left under stirring at 50° C. for 30 minutes, then at room temperature for 1 hour. The solid is filtered through a Büchner funnel, washing the cake with 50 mL of toluene.

The resulting crystal is dried under vacuum at the temperature of 60° C., providing intermediate IVb in a 92% yield (19.5 g, 69.5 mmol) and HPLC purity >99.9%.

$^1$H NMR (300 MHz, CDCl$_3$) 1.80-2.25 (m, 4H), 2.60 (m, 2H), 2.70 (d, 3H), 3.60 (s, 3H), 5.95-6.21 (dd, 2H), 7.23 (s, 1H), 7.44 (t, 1H), 7.63 (t, br 1H).

Example 4: Synthesis of Intermediate IVc

Intermediate III (30 g, 112.6 mmol) is suspended in HMDS (150 mL, 715.6 mmol) and placed under nitrogen. TFA (2 mL, 25.9 mmol) is dropped into the suspension in 15 minutes, ensuring that the temperature does not exceed 30° C. The reaction mass is heated to reflux (about 130° C.) for 4 hours, followed by a solvent change with toluene; abundant crystal precipitation is observed. The mixture is left to cool slowly overnight, then filtered through a Bulmer funnel, washing the cake with 30 mL of toluene. The resulting crystal is dried under vacuum at the temperature of 50° C., providing intermediate IVc in a 85% yield (32.3 g, 95.7 mmol).

Example 5: Synthesis of Intermediate IVd

Intermediate III (50 g, 187.8 mmol), diphenylcarbonate (48.2 g, 225.0 mmol) and DBN (2.3 mL) are suspended in 5 volumes of DMSO, and placed under nitrogen.

The reaction mass is heated at 90° C. for 20 hours. The temperature is reduced to 20° C. and water is added, causing the product to precipitate. The precipitate is filtered through a Buchner funnel, washing the cake with water.

The wet product is taken up with 10 volumes of toluene and left under stirring at room temperature for at least 6 h under nitrogen. The product is filtered through a Buchner funnel, washing the cake with toluene.

The resulting crystal is dried under vacuum at the temperature of 50° C., providing intermediate IVd in 87% yield (56.3 g, 164.1 mmol).

$^1$H NMR (300 MHz, CDCl$_3$) 1.95-2.42 (m, 4H), 2.80 (m, 2H), 2.74 (d, 3H), 6.16-6.33 (dd, 2H), 6.94 (d, 2H), 7.26 (t, 1H), 7.40 (m, 3H), 7.55 (t, 1H), 7.70 (t, br, 1H).

Example 6: Synthesis of Apalutamide

Intermediates IVa-d (40.3 mmol) and intermediate V (12 g, 52.3 mmol) are dissolved in a mixture of isopropyl acetate (15 mL) and DMSO (7.5 mL). The mixture is placed under nitrogen and heated to reflux (about 90° C.) for about 17 hours. The reaction is cooled to 60° C., and 67 mL of isopropyl acetate is added. The organic phase is washed twice with 150 mL of a 5% NaCl aqueous solution by weight, and once with 150 mL of water. The organic phase is then dried by successive distillations of isopropyl acetate, reducing it to the residual volume of 22.5 mL.

The organic phase is reduced to residue in the Rotavapor, and the product is purified by silica-gel column chromatography with hexane/isopropanol (7:3) as eluent.

The product is isolated in 30-35% yields and 80% HPLC purity.

$^1$H NMR (300 MHz, CDCl$_3$) δ 1.73 (m, 1H), 2.28 (m, 1H), 2.50-2.80 (m, 4H), 3.07 (d, 3H), 6.73 (m, 1H), 7.13-7.29 (dd, 2H), 8.28-8.38 (dd, 2H), 9.08 (d, 1H)

Example 7: Synthesis of Intermediate III

Compound I (100 g, 0.594 mol) is suspended in 300 mL of dioxane. TEA (250 mL, 3.59 mol) is added by pouring in a thin stream. The system is placed under nitrogen, and heated to 60° C. A solution of intermediate II (160 g, 0.90 mol) in 150 mL of dioxane is prepared separately.

The solution of compound II is added to the suspension in the reactor and left to react for about 20 hours. The mixture is cooled to 15° C. and filtered through a Büchner funnel, washing the cake twice with 100 mL of dioxane each time. The resulting product is suspended in 1200 mL of water, 1M HCl is added until a pH<3 is reached, and the resulting suspension is then filtered through a Büchner funnel, washing the cake twice with 200 mL of water each time.

The crystal thus isolated is dried under vacuum at the temperature of 60° C., providing intermediate III in a 76% yield (120 g, 45.1 mmol) and 99.6% HPLC purity.

$^1$H NMR (300 MHz, CDCl$_3$) δ 15.3 (m, 4H), 2.58 (t, br, 2H), 2.73 (s, 3H), 6.00 (m, 1H), 6.22 (s, 1H), 7.17 (s, 1H), 7.46 (s, 1H), 7.65 (d, 1H), 12.63 (m, 1H).

Example 8: Synthesis of Intermediate IVd

Intermediate III (50 g, 187.8 mmol), diphenylcarbonate (48.2 g, 225.0 mmol) and DBN (2.3 mL) are suspended in 5 volumes of DMSO, and placed under nitrogen.

The reaction mass is heated at 65° C. for at least 20 hours. The temperature is lowered to 20° C., and a mixture of water and acetone is added, causing the product to precipitate. The mixture is left under stirring until abundant precipitation forms, and filtered through a Büchner funnel, washing the panel with water.

The wet product is taken up with 10 volumes of an 8/2 mixture of dimethyl carbonate/cyclohexane and left under stirring at room temperature for at least 6 h under nitrogen. The mixture is filtered through a Buchner funnel, washing the cake with cyclohexane.

The resulting crystal is dried under vacuum at the temperature of 50° C., providing intermediate IVd in 87% yield (56 g, 163.3 mmol).

$^1$H NMR (300 MHz, CDCl$_3$) 1.95-2.42 (m, 4H), 2.80 (m, 2H), 2.74 (d, 3H), 6.16-6.33 (dd, 2H), 6.94 (d, 2H), 7.26 (t, 1H), 7.40 (m, 3H), 7.55 (t, 1H), 7.70 (t, br, 1H).

Example 9: Synthesis of Apalutamide

Intermediates IVa-d (146 mmol) and intermediate V (67 g, 292 mmol) are dissolved in a mixture of isopropyl acetate (150 mL) and DMSO (5.2 mL). The mixture is placed under nitrogen and heated to reflux (about 90° C.) for about 17 hours. The reaction mass is cooled to 60° C. and crystallised from a suitable organic solvent, producing 65-68 g of crude Apalutamide which, suitably recrystallised, provides 50-52 g of Apalutamide with a purity exceeding 99%, and 72-73% yield.

$^1$H NMR (300 MHz, CDCl$_3$) δ 1.73 (m, 1H), 2.28 (m, 1H), 2.50-2.80 (m, 4H), 3.07 (d, 3H), 6.73 (m, 1H), 7.13-7.29 (dd, 2H), 8.28-8.38 (dd, 2H), 9.08 (d, 1H).

The invention claimed is:

1. A process for the preparation of Apalutamide which comprises (a): alkylating in dioxane 4-amino-2-fluoro-N-methyl-benzamide of formula I

I with an alkyl halide of formula II

II wherein X is bromine to give the compound of formula III

III (b): activating the carboxyl group of the compound of formula III, via the formation of the compounds of formula IV

IV wherein Y is (c): condensating the activated product IV obtained in step (b) with the isothiocyanate of formula V

V to give crude Apalutamide;

(d): purifying the crude Apalutamide obtained in step (c).

2. The process according to claim 1 wherein intermediate III is converted to one of the esters of formula IVa, IVb, IVc or IVd IVa -continued

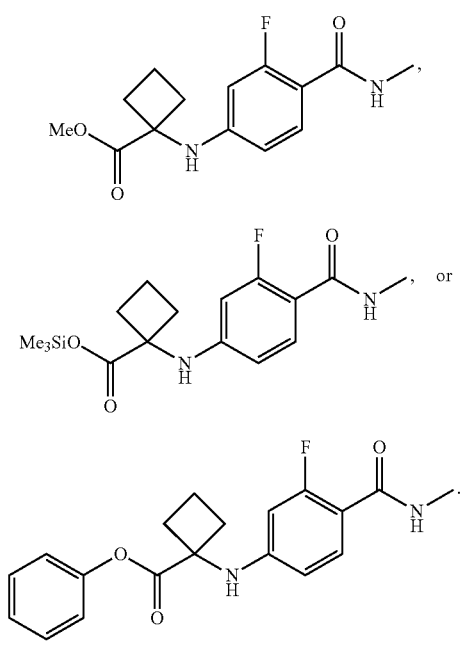

IVb

IVc

IVd

3. The process according to claim 1 wherein step (b) is conducted in a solvent selected from alcohols, dichloromethane, toluene, dimethyl carbonate and dimethylsulphoxide.

4. The process according to claim 1 wherein step (c) is conducted in a solvent selected from acetonitrile, ethyl acetate, isopropyl acetate, isobutyl acetate, dimethylsulphoxide and dimethylformamide.

5. Esters of formula IVa, IVc or IVd

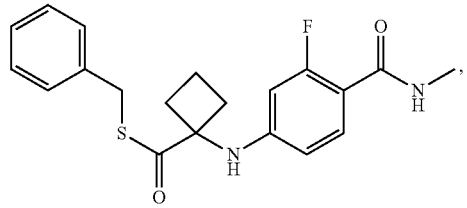

IVa

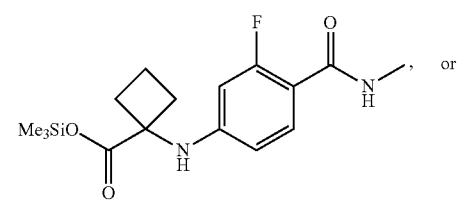

IVc

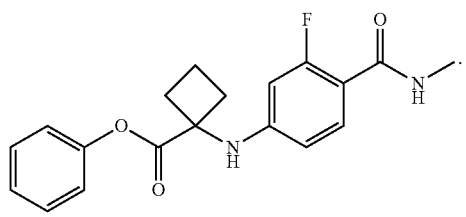

IVd

6. The process according to claim 3 wherein step (b) is conducted in dimethyl carbonate or dimethylsulphoxide.

* * * * *